United States Patent
Platzer et al.

(12)

(10) Patent No.: US 6,381,014 B1
(45) Date of Patent: Apr. 30, 2002

(54) DEVICE FOR ANALYZING GASEOUS SAMPLES

(75) Inventors: Bernhard Platzer, Rosenberggürtel 46, Graz (AT), 8010; Günter Knapp, Graz (AT)

(73) Assignee: Bernhard Platzer, Graz (AT)

( * ) Notice: Subject to any disclaimer, the term of this patent is extended or adjusted under 35 U.S.C. 154(b) by 0 days.

(21) Appl. No.: 09/389,348

(22) Filed: Sep. 3, 1999

Related U.S. Application Data

(63) Continuation of application No. PCT/AT98/00047, filed on Mar. 3, 1998.

(30) Foreign Application Priority Data

Mar. 4, 1997 (AT) .............................. A367/97

(51) Int. Cl.[7] .............................. G01N 21/73
(52) U.S. Cl. ...................... 356/316; 356/417
(58) Field of Search .................. 356/311, 313, 356/316, 417

(56) References Cited

U.S. PATENT DOCUMENTS

| | | | |
|---|---|---|---|
| 3,508,106 A | 4/1970 | Vecsernyes ................ 313/231 |
| 3,685,911 A | 8/1972 | Dahlquist et al. .......... 356/313 |
| 3,887,280 A | 6/1975 | McLean ..................... 356/316 |
| 4,517,824 A | 5/1985 | Quimby ........................ 73/23 |
| 4,654,504 A | 3/1987 | Sullivan et al. ............. 219/121 |
| 4,776,690 A | 10/1988 | Quimby ....................... 356/72 |
| 5,009,099 A | 4/1991 | Wells et al. .................... 73/1 |
| 5,151,371 A | 9/1992 | Quimby et al. ............. 436/127 |
| 5,153,519 A | 10/1992 | Wentworth et al. ......... 324/464 |
| 5,394,090 A | 2/1995 | Wentworth et al. ......... 324/464 |
| 5,394,091 A | 2/1995 | Wentworth et al. ......... 324/464 |
| 5,394,092 A | 2/1995 | Wentworth et al. ......... 324/464 |

FOREIGN PATENT DOCUMENTS

| DE | 3840106 | 6/1989 |
|---|---|---|
| DE | 3942375 | 6/1991 |
| DE | 4110343 | 10/1991 |

OTHER PUBLICATIONS

L. Hara et al, Analytical Chemistry No. 4, "Rotating arc direct current plasma as an emission . . . ", Apr. 4, 1985, pp. 841–845.
D. Slinkman et al, Analytical Chemistry No. 15, "Magnetron rotating direct current . . . ", Aug. 1, 1990, pp. 1656–1661.
E. L. Grove, Analytical Spectroscopy Series, "Analytical emission spectroscopy", 1972, pp. 191–213 and 246–251.

*Primary Examiner*—F. L. Evans
(74) *Attorney, Agent, or Firm*—Jacobson Holman, PLLC

(57) ABSTRACT

The invention relates to a device for analyzing gaseous samples comprising a device for generating a plasma, a feeding device for the sample to be analyzed and at least one detector unit which in particular comprises at least one interference filter, a lens arrangement and a photodetector for detecting radiation, especially atomic emission or molecular emission, emitted by the sample to be analyzed. According to the invention, said device for generating the plasma is made up of two in particular ring- or disk-shaped parallel, interspaced electrodes, wherein each electrode has one essentially centrical, especially circular through-opening, and an isolator positioned between said electrodes, said isolator having a particularly circular through-opening for confining the plasma. In addition the invention provides for an optical unit, in particular a collimator lens, to be placed between said device for generating the plasma and the detector unit for forming a parallel ray beam.

29 Claims, 7 Drawing Sheets

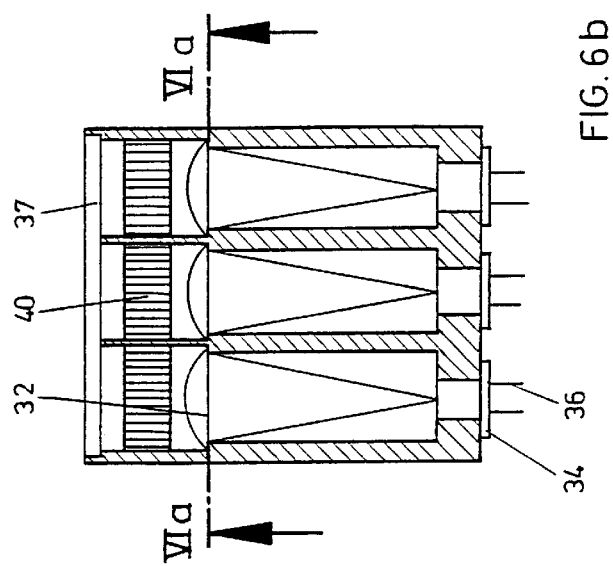
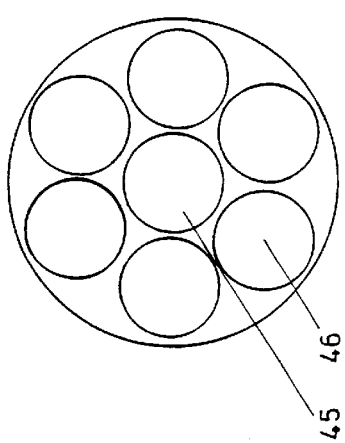
FIG. 6b
FIG. 6a
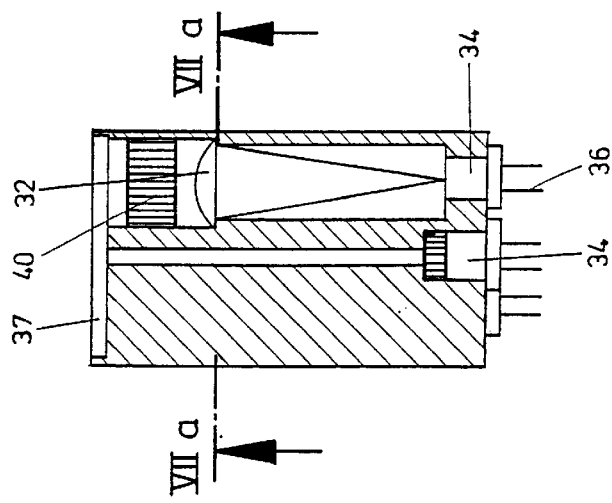
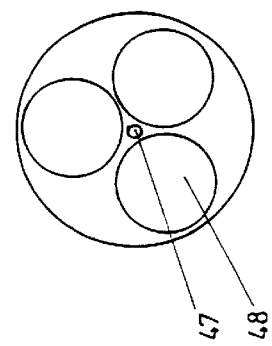
FIG. 7b
FIG. 7a

DEVICE FOR ANALYZING GASEOUS SAMPLES

This is a continuation application of PCT/AT98/00047, filed on Mar. 3, 1998.

BACKGROUND OF THE INVENTION

The present invention relates to a device for analyzing gaseous samples comprising a device for generating a plasma, a feeding device for the sample to be analyzed and at least one detector unit, which in particular comprises at least one interference filter, a lens arrangement and a photodetector for detecting radiation, especially atomic emission or molecular emission, emitted by the sample to be analyzed.

A device for analyzing gaseous samples of this kind has for example been disclosed in U.S. Pat. No. 5,009,099, wherein a plasma generator, to which the sample can be introduced, is followed by a detector unit consisting of a multitude of photodetectors wherein the object of this known device is in particular to provide background correction in a plasma gas chromatography detector.

A detector unit for use in a device, as mentioned above, to record the radiation emitted from a sample to be analyzed has in its own been disclosed for example in DE-OS 39 42 375, wherein it is the object of this known device to simultaneously record several wavelength ranges of a polychromatic radiation, with one detector for each of the wavelength ranges considered. In this known embodiment the detector or each detector unit is formed of an interference filter, a lens arrangement and a following photodetector with an according readout electronics.

A modified sensor for a portable analysis instrument can be found for example in DE-A 38 40 106, wherein a plurality of folding mirrors is employed.

For the production of a plasma for various applications it is furthermore referred to for example U.S. Pat. No. 4,654,504, U.S. Pat. No. 5,394,090, U.S. Pat. No. 5,394,091, U.S. Pat. No. 5,394,092 or U.S. Pat. No. 5,153,519, wherein in these known embodiments various designs of microwave and RF plasma generators are proposed to provide a plasma for various applications or analytical procedures. Problematic with these known devices is the coupling of electromagnetic energy into the plasma gas, wherein the employed power is usually around several hundred watts. Therefore the power to be coupled is very high, so that adequate heat dissipation has to be provided in immediate vicinity of the produced plasma, to avoid damage to parts of the apparatus. For this purpose not only parts of the apparatus must be made of an electrically non-conducting, high-temperature resistant material to separate the gas or plasma from the remaining parts of the apparatus, but furthermore by providing such enclosing elements for the plasma, there results mostly an enormous requirement of space for the corresponding cooling devices, which renders the production of a plasma of low spatial spread more difficult or even impossible.

In the context of producing the plasma and in particular the use of additive gases and the correspondingly used plasma gases it can furthermore be referred to U.S. Pat. No. 4,776,690, U.S. Pat. No. 5,151,371, U.S. Pat. No. 3,887,280 or U.S. Pat. No. 4,517,824, where the use of various plasma gases and their additive gases is described in the context of specific applications in the analysis of gaseous samples.

Regarding the selection of plasma gases the use of a noble gas, and in particular helium or argon, has been for example disclosed in DE-A 41 10 343 or U.S. Pat. No. 5,394,092.

SUMMARY OF THE INVENTION

Starting from a device of the kind mentioned above and taking into account the disadvantages of known devices and designs, it is the object of the present invention to provide a device for the analysis of gaseous samples by which it is possible, with a simple and compact design and low plasma power and a small detector volume, which favors use of the device according to the invention in mobile or portable instruments, to achieve a correspondingly high accuracy and reliability of results on the samples to be analyzed.

To solve this problem, the device of the subject invention is essentially characterized in that the device for generating the plasma is made up of two in particular ring- or disk-shaped parallel, interspaced electrodes, each having one essentially centrical, in particular circular through-opening, and an isolator having a particularly circular through-opening for confining the plasma and that between said device for generating the plasma and the detector unit an optical unit, in particular a collimator lens for generating a parallel ray beam is provided. By forming, according to the invention, the device for generating a plasma from at least one isolator, which is positioned between parallel interspaced, in particular ring- or disk-shaped electrodes, wherein the electrodes and the interposed isolator forming the plasma producing unit are each provided with an essentially centrical opening, the establishment a plasma of low spatial spread and defined position is successfully achieved, wherein the dimensions of the plasma can be selected according to the various requirements. Furthermore it is possible to achieve through said isolator, in the particularly circular through-opening of which said plasma is produced and maintained, in a simple way and without the provision of (additional) confining elements, such as tubes, or additional means for heat dissipation, a safe confinement of said plasma and simultaneously securing heat dissipation from the immediate vicinity of said plasma. Through said in particular ring- or disk-shaped electrodes, which are positioned at both sides of said isolator and the through-openings of which are aligned with respect to each other, the supply of the energy necessary for the ignition and maintenance of said plasma is successfully achieved in a very small volume, such that overall a simple method for the production of such a low-power plasma, in particular noble gas plasma, can be provided at low power uptake and low gas consumption. Apart from the device for generating a plasma being formed from simple elements and overall small dimensions, it is possible to provide, by combination with the further provided optical unit, in particular a collimator lens for the formation of a parallel ray beam, and at least one detector unit an altogether compact, easy to use and simple to maintain overall design of the design according to the invention.

According to a preferred embodiment of the device for analyzing gaseous samples according to the invention, the design is such that, viewed with respect to the direction of plasma gas flow, another isolator with a through-opening, which is essentially equivalent to said through-opening of said isolator positioned between said electrodes, is positioned upstream of said first electrode. By an isolator positioned upstream, with respect to the direction of supply of plasma gas, a shielding action towards the direction of supply of plasma gas and sample is achieved, such that an impairment of the plasma gas to be introduced, and the sample to be introduced and subsequently analyzed, can be prevented. At this in particular the provision of a suitably small through-opening in said upstream isolator, which is essentially equivalent to the through-opening of the isolator positioned between the electrodes, in which the plasma is formed and confined, it is possible to achieve protection of the sample against decomposition or polymerization, caused by UV radiation or extended glow discharges, before reaching the plasma.

The isolator positioned upstream of said plasma could, if this side is at ground potential, be made of metal, for example Pt/Ir. To reduce the number of components it is proposed in another preferred embodiment that the first electrode, viewed with respect to the direction of gas flow, and the isolator positioned upstream of it are combined into one single component, and that the through-opening corresponding to the through-opening confining the plasma is followed by a preferably conically expanding section.

To protect operative equipment which is positioned downstream of the system of said electrodes and said interposed isolator it is proposed to position an additional isolator downstream of the, viewed with respect to the direction of gas flow, second electrode, the through-opening of said isolator being preferably slightly smaller than the through-opening of the adjacent electrode, which constitutes another preferred embodiment of the device according to the invention. By selecting the through-opening of the downstream isolator appropriately, protection of the electrode surface is improved. Furthermore the fact that the through-opening of the electrodes is considerably larger than the inner diameter of the through-opening of at least the isolator confining and defining the plasma, ensures that a sufficient amount of the radiation emitted by the sample to be analyzed, in particular atomic or molecular emission, can escape from the plasma production unit for subsequent detection. In this context it is proposed according to a particularly preferred embodiment that the internal diameter of the through-opening in the isolator positioned downstream of said electrodes is at least two times the internal diameter of the through-opening in the isolator positioned upstream of said electrodes.

To simplify the assembly of the device to generate the plasma, such that the central part for plasma production being constituted by the electrodes and the isolator can be for example pre-manufactured, it is proposed according to another preferred embodiment that said electrodes and isolators are either pressed together mechanically, for example by spring action, or are bonded together by known techniques of metal-ceramic bonding, in particular by soldering in vacuum or hydrogen atmosphere.

For a particularly simple mounting of the plasma production unit it is further preferably proposed that said electrodes and said isolator or isolators are held in at least one fixture and are mounted in a gas-tight manner, wherein in particular due to the fact that the spatial dimensions of the plasma are extremely small, it is further preferably proposed that the fixtures are equipped with centering mounts for said electrodes and/or isolators. In such a way a pre-assembled unit or device for producing a plasma can be easily replaced as a whole, wherein the centering mounts of the fixtures enable precise and reliable positioning relative to the remaining elements, and in particular relative to the inlet of the plasma gas and the sample to be analyzed as well as the downstream optical unit and detector unit.

As already mentioned above, the implementation of a compact device for generating a plasma, which can be operated at a suitably low power level, renders the provision of costly accessory equipment unnecessary, wherein in particular the provision of additional, often bulky cooling devices can be eliminated. For an orderly exhaust of the plasma gas and/or the supply of an additive gas in the region of plasma production it is, according to the invention, furthermore preferably proposed that said fixtures have outlets or purging holes, in particular for supplying an additive gas to the plasma gas. Regarding the exhaust of the plasma gas it can be further provided that the cavity housing said electrodes and/or said fixtures can be purged with a purge gas, according to a further preferred embodiment of the device according to the invention. In particular the provision of a purge, for the cavity housing the electrodes and/or said fixtures, with a purge gas produces benefits with respect to requirements of gas-tightness for the electrode assembly, as in this case the specifications for gas-tightness for the device for producing the plasma can be lowered. Furthermore, by such a purge gas the plasma exhaust gases can be exhausted in a controlled way and, if needed, consequently be filtered, wherein for the exhaust of plasma gases by such a purge gas attention must be paid to sufficiently dilute the plasma gas with a plasma-impeding gas to prevent uncontrolled discharges in the region outside the device for plasma production, and in particular in the region of energy supply. Similarly it may be provided that the space between said device for generating the plasma and said optical unit can be purged with a purge gas, according to another preferred embodiment of the device according to the invention.

As already mentioned above, the device for generating a plasma with narrow spatial dimensions, provided in the device according to the invention, enables the production of an accordingly low-power plasma, wherein according to the invention it is provided in this context that the power of the plasma is below 50 W, and preferably between 3 and 30 W, such that sufficient heat dissipation can be accomplished without the provision of costly cooling devices. For an array of plasma discharges said power is provided for each single discharge.

In order to accomplish a stable plasma with simple and cost-effective electronic components the device according to the invention is preferably characterized in that the excitation or operating frequency for said device for generating the plasma is selected to be at least 5 kHz, preferably in the range of 50 kHz to 5 GHz, and more preferably above 10 MHz.

As to the plasma gas it is preferably proposed for applying the device according to the invention that the plasma gas is selected from helium or argon. In particular helium is preferred because of its low atomic mass, since it hardly causes erosions on the electrodes.

According to a further preferred embodiment it is proposed that the pressure of the plasma gas is selected to be at least 0.01 bars, preferably between 0.1 and 5 bars, so that particularly around atmospheric pressure a low-power plasma for the analysis of samples can be provided.

For the formation of a plasma it may be provided besides the use of plasma gas in various applications that an additive gas is admixed to said plasma gas at a level of at most 35 vol.-%, preferably less than 25 vol.-%, wherein said additive gas is preferably selected from $CO_2$, $N_2$, air, water vapor, hydrogen and oxygen, according to another preferred embodiment. Furthermore a vaporized compound, in particular water vapor, may be provided by diffusion or permeation in a thermostatted device close to the plasma, whereby the generally difficult transport of the vapor to the plasma through for example heated ducts can be avoided.

For the simultaneous evaluation or analysis of different wavelength ranges it is proposed according to a further preferred embodiment that several detector units are arranged side by side and are illuminated by the parallel ray beam, wherein it is provided according to a particularly preferred embodiment that a multitude of detector units are positioned each at the same distance from and around a centrally positioned detector unit. By providing a multitude of detector units side by side in the emitted ray bundle it is possible to obtain simultaneous, fast and reliable analysis results. Herewith the interference filters assigned to a single detector unit can be used in a mounting which ensures the best possible resolution or transmission curve, wherein the arrangement of multiple detector units side by side furthermore enables a very simple assembly and if needed a simple interchange of single detector units or element combinations, which each consist of a filter, a lens assembly and a photodetector with possibly integrated signal electronics. The use of only a single detector unit can be considered for the analysis of elements such as carbon, hydrogen, oxygen or nitrogen, for which a spectral background correction is not required, since essentially the baseline is dominated by a measurable signal, caused by contamination. The arrangement of multiple detector units side by side can be used for the analysis of a corresponding number of different elements, or for example also to analyze multiple different lines of a single element, to increase selectivity, wherein generally wavelength combinations covering a very wide range, as well as for special applications having arbitrarily close spacing, are possible. For the determination of a correction signal it may be provided according to a particularly preferred embodiment that the centrally positioned detector unit has an area smaller than that of the other detector units, wherein in such a centrally positioned detector unit of reduced area for example oxygen can be measured for correction purposes.

For an accordingly efficient use of the emitted radiation, which can be very positively affected by suitable selection of the through-opening of the downstream isolator in the device for plasma generation, it is proposed according to a further preferred embodiment that collimator lens is formed by an aspheric collimator lens of high aperture.

For special applications a separation of the device for plasma generation from the actual analysis or detector device may be advantageous, wherein it is proposed that between said device for generating the plasma and the at least one detector unit a fiber-optic link is provided, according to another preferred embodiment of the device for analyzing gaseous samples according to the invention.

For a further optimization of space requirement it may be provided according to a further preferred embodiment, that between said device for generating the plasma and the at least one detector unit a deflecting or folding mirror is provided.

When using the device for analysing gaseous samples according to the invention it is further possible to use a carbon signal to protect the plasma from overload, wherein in the case of overload of the plasma with organic substances soot may be formed in the discharge zone and, due to the electrical conductivity of the soot, may create problems. Such the continuous measurement of an appropriately scaled carbon signal from the plasma may be used to switch off the plasma for a predetermined time when a certain threshold is exceeded, whereupon the plasma may be re-ignited automatically. Such an automatic control, which may also take into consideration the ratio of carbon to oxygen, can be implemented easily by providing the appropriate electric or electronic circuitry. In this context it is preferably proposed that said device for generating the plasma is coupled to an automatic control for switching off said device for generating the plasma as soon as a threshold value for the carbon signal is exceeded, and subsequent re-ignition of the same.

Further, by providing a multiple detector units positioned side by side a relatively simple background correction can be implemented, wherein again the large solid angle, which can be obtained by suitable dimensioning of the exit aperture of the device for plasma generation, enables the simultaneous measurement of a multitude of wavelength ranges and the resulting assistance in background correction.

Signal processing of the various signal and background intensities obtained by separate measurement with photodetectors can further be achieved with the help of at least partially known evaluation circuitry or microcomputers.

BRIEF DESCRIPTION OF THE DRAWINGS

The device according to the subject invention is subsequently illustrated by means of embodiments shown in the attached schematic drawings.

FIGS. 6a and 6b show partial views of a multitude of detector units in a device according to the invention to analyze gaseous samples, wherein the schematic view according to FIG. 6a represents a section along line VIa-VIa of FIG. 6b;

FIGS. 7a and 7b show, in a representation analogous to FIG. 6a and 6b, a modified embodiment of the arrangement of detector units in a device according to the invention to analyze gaseous samples.

DETAILED DESCRIPTION OF THE PREFERRED EMBODIMENTS

Figure 1:
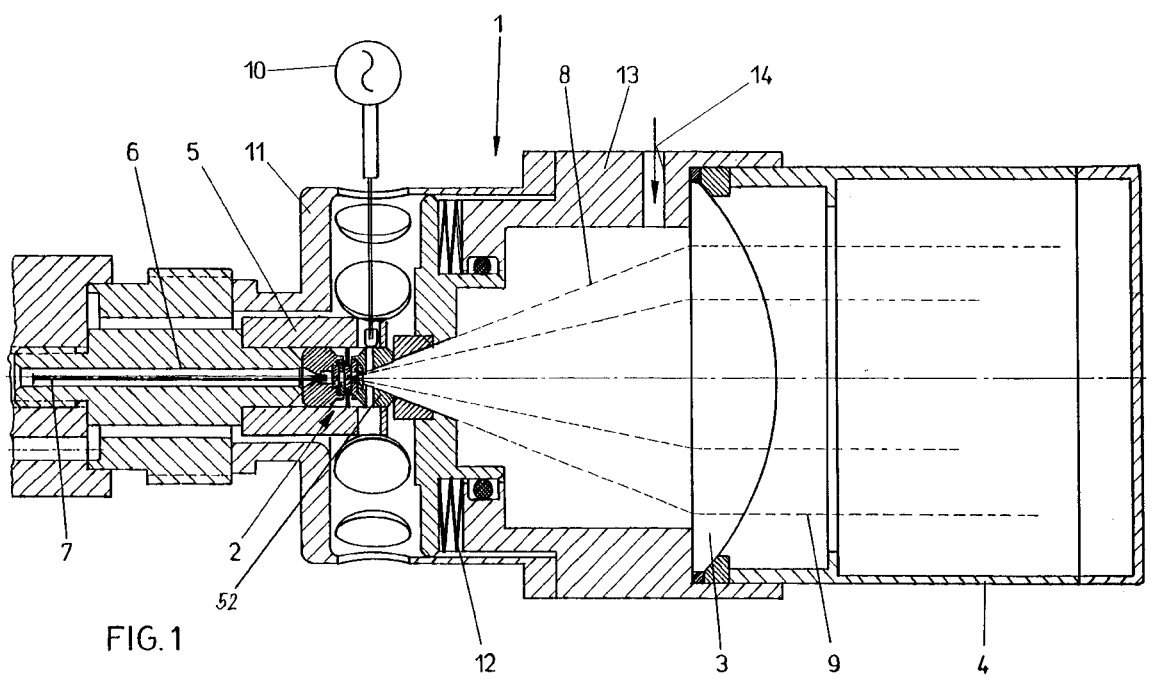
FIG. 1 shows a sectional view of a first embodiment of a device according to the invention to analyze gaseous samples.
Figure 2:
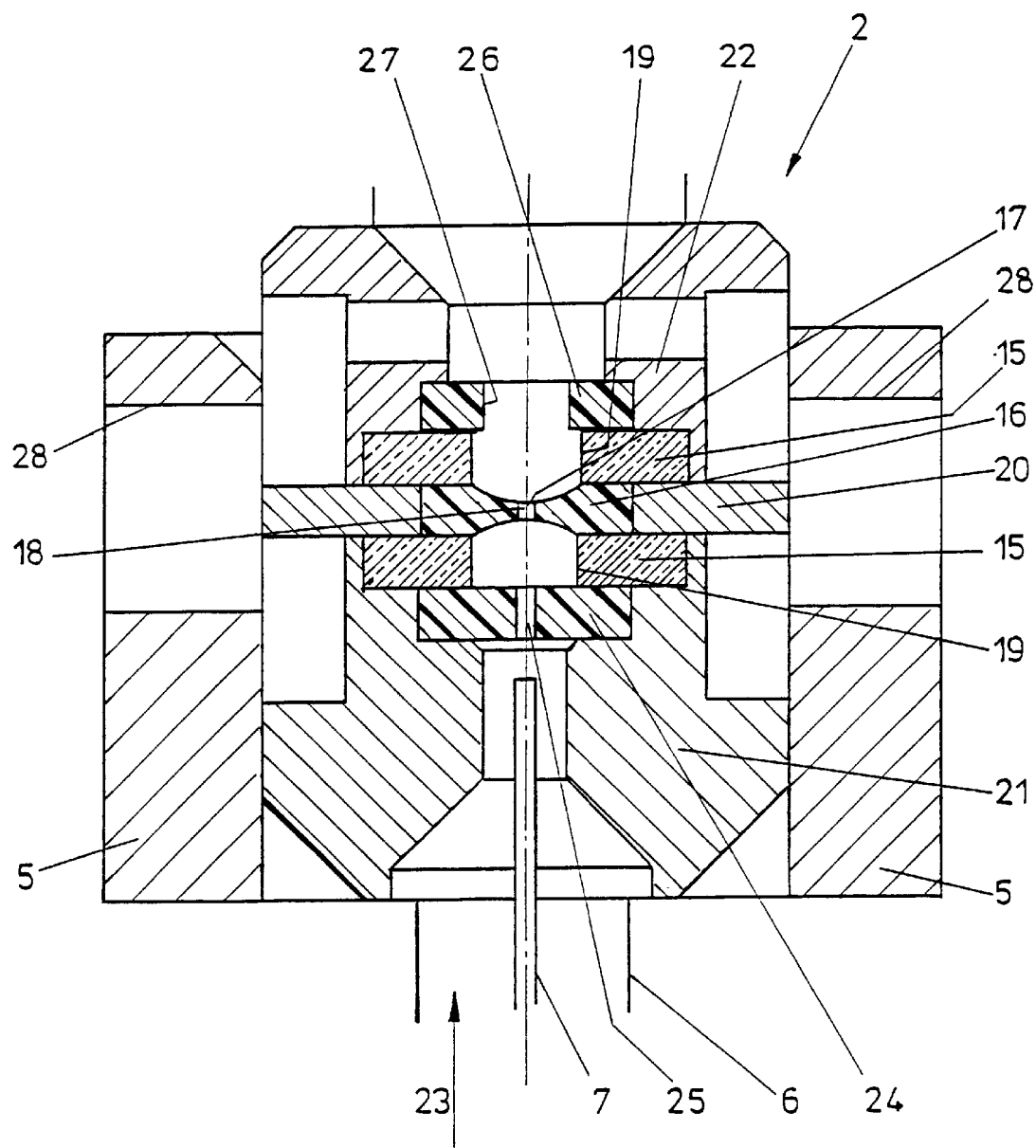
FIG. 2 shows in enlarged scale a sectional view of a device to generate a plasma in the device according to FIG. 1.

In FIG. 1 a device for analyzing gaseous samples is schematically designated as 1, which is formed from a device for generating a plasma generally designated as 2 and shown in detail in an enlarged scale in FIG. 2, an optical unit 3, in particular a collimating lens, and a unit 4, only schematically outlined in FIG. 1, comprising at least one detector unit. Such detector units are shown in the following figures and in particular, in detail, in FIGS. 6a and 6b, 7a and 7b.

The device 2 for generating a plasma, shown in more detail in FIG. 2, is accommodated and held in suitable mounts or fixtures, wherein the mounts adjacent to device 2 are designated with 5. Further both an inlet 6 for the plasma gas, as well as a centrally positioned inlet 7 for the sample to be analyzed subsequently, are outlined schematically.

The radiation emitted from the device 2 for generating a plasma is confined essentially by the schematically outlined cone 8, for example an isolator 52 with a suitable shape, and comes in turn to the optical unit 3, whereby a parallel ray beam 9 is formed, which can be analyzed in the ensuing detector unit 4 as it will be described in more detail with reference to subsequent figures.

In the schematic representation according to FIG. 1 furthermore an energy supply 10 for the device 2 for generating a plasma is schematically outlined and it can further be seen that the housing component 11, which accommodates the device 2, the inlets 6 and 7, is connected with another component 13 of the housing, which accommodates the optical unit 3 and the detector unit 4, by interposed spring washers 12. An inlet opening for the introduction of a purge gas into the optical unit 3 is outlined as 14.

From the representation according to FIG. 2 it can be seen that the device 2 for generating a plasma comprises two parallel, interspaced, disk- or ring-shaped electrodes 15, between which any isolator 16, made for example of ruby, sapphire or generically any poorly or non-conducting oxide ceramic, is positioned. Said isolator 16 has a through-opening 17, in which subsequently a plasma 18 of exactly defined dimensions is formed. Each electrode 15 has an essentially circular through-opening 19, wherein both said through-opening 17 of said isolator 16 and said through-opening 19 of the electrodes 15 are aligned to each other. Furthermore, as can be clearly seen from FIG. 2, said through-openings 19 of the electrodes 15 are significantly larger than the through-opening 17 of said isolator 16. Both said electrodes 15 and said isolator 16 as well as another isolator 20, surrounding the isolator 16, which prevents spark formation at the outside of the electrodes 15, are accommodated in fixtures 21 respectively 22, to form an adequately tight and compact assembly of the device 2 for generating said plasma, which can for example be pre-assembled and accommodated in the fixtures designated as 5. Said electrodes 15 are furthermore, in a way not specifically shown, such as a spring-loaded contact pin, connected with a generator for the supply of energy for ignition and maintenance of the plasma 18 to be formed in the through-opening 17 of said isolator 16.

Furthermore in FIG. 2 again the inlet for the plasma gas is designated as 6 and a sample inlet is designated as 7, whereby said inlet 7 may be formed for example from a quartz capillary tube. Through inlet 6, as already mentioned above, a plasma gas, such as for example helium or argon, and if need be also an additive gas such as for example $CO_2$, $N_2$, air, hydrogen, water vapor or oxygen, is supplied to the region of the electrodes 15 and said isolator 16 positioned between them.

From FIG. 2 it can be further seen, that viewed with respect to the direction 23 of flow of sample and plasma gas, another isolator 24 with a through-opening 25, the dimensions of which are essentially equivalent to the dimensions of said through-opening 17 of said isolator 16 confining the plasma, is positioned upstream of the first electrode 15. Said isolator 24, positioned upstream with respect to flow 23, serves essentially the purpose of avoiding arcing of the plasma 18 into inlets 6 or 7 and damaging the surrounding elements. It can be further seen from FIG. 2, that an additional isolator 26 is positioned downstream of the second electrode 15, viewed with respect to the direction 23 of plasma gas flow, the through-opening 27 of it being slightly smaller than the inner diameter 19 of the adjacent electrode 15, wherein said through-opening 27 of this downstream isolator 26 significantly exceeds the inner diameter of through-opening 17 of isolator 16, such that an accordingly wide cone of emitted radiation and hence an accordingly large yield of the radiation subsequently to be detected and analyzed is achieved, as this is schematically outlined by said cone 8 in FIG. 1.

Furthermore exhaust- or purge-openings 28 are indicated in the region of the fixtures or mounts 5, 21 and 22, through which the addition of purge gases or also the additional supply of additive gases to the plasma gas is enabled to achieve a suitable gas distribution in the region of plasma generation.

The diameter of the through-opening 17 in the isolator 16, which is positioned between the electrodes 15 and defines the dimensions of the plasma to be formed, can be less than 0.5 mm. The inner diameter of the through-openings 19 of the electrodes 15 on the other hand is for example 0.5 to 1 mm or above. The thickness of the electrodes 15 as well as the isolators 16, 24, and 26 can be for example 0.5 mm, wherein the taper of the isolator 16 results in an accordingly reduced thickness of its central region.

It is therefore possible, with simple means, to provide a compact device for generating said plasma, by which the spatial dimensions of the plasma 18 are very small and precisely definable, such that at atmospheric conditions a low-power plasma with a power of for example below 50 W, and preferably between 3 and 30 W, at excitation frequencies higher than 5 kHz, for example in the range of 50 kHz to 5 GHz, and preferably higher than 10 MHz can be formed. Furthermore the pressure of the plasma gas is selected to be at least 0.01 bars, but preferably between 0.1 and 5 bars. Due to the low power of the plasma produced in the device 2 it is furthermore possible to safely dissipate the resulting heat through the isolator 16 and the subsequent isolator 22, wherein an additional cooling-effect is possible through supply of an exhaust or purge gas through the openings 28 in said fixtures or mounts 5, 21 and 22. Providing the fixtures 21 and 22 as well as said additional isolator 20 surrounding the isolator 16, enables secure positioning of the single elements 15, 16, 20, 24, and 26, having only small dimensions, of the device 2 for generating a plasma, wherein furthermore the fixtures 21 and 22 are provided with centering mounts, or serve directly themselves as centering when mounting the device 2 in the fixtures 5.

To achieve adequate tightness of the device 2 between the several elements, i.e. in particular between the electrodes 15 and the isolators 16, 24, and 26 it may be provided that the fixtures 21 or 22 as well as the electrodes 15 are appropriately coated, and furthermore the joining of the electrodes 15 with the isolators 16, 24, and 26 can be effected for example mechanically and by providing appropriate springs, or alternatively known techniques of metal-ceramic bonding can be employed to achieve an appropriate tightness. In the case that the requirements on tightness should not be set too high, it is further possible by adequate purging of the device 2 to moreover orderly remove gases or reaction products leaking from the device 2 for generating a plasma.

Figure 3:
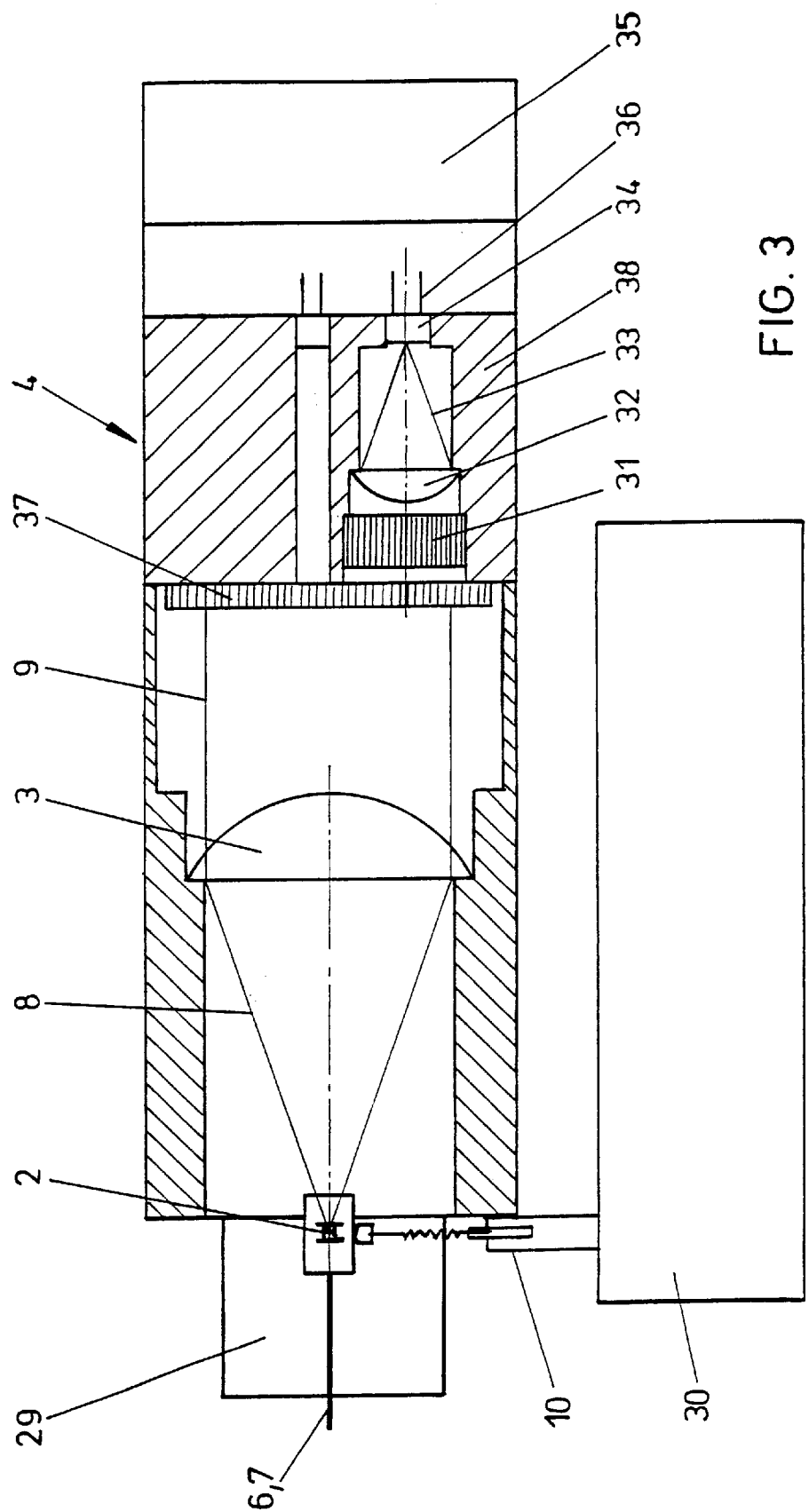
FIG. 3 shows a schematic sectional view of a modified embodiment of a device according to the invention to analyze gaseous samples.

In the modified embodiment shown in FIG. 3 the reference numbers of the previous figures for the same components have been retained. So again 2 schematically designates a device for generating a plasma, wherein the supply of plasma gas as well as the sample to be analyzed again is through inlets 6 and 7. In this embodiment it is provided that in the region of the inlets 6, 7 a heating appliance, schematically designated with 29, can be put to use. The supply of RF energy is effected again through a line schematically designated as 10, from a generator 30.

The device 2 for generating a plasma is again followed by an optical unit, in particular a collimating lens 3, which serves to form a parallel ray beam 9, which hits a detector unit, again designated as 4. In this detector unit an interference filter 31 and a lens assembly 32 are provided, whereafter the beam to be detected 33 hits a photodetector 34, whose output connections to an electronic circuit schematically designated as 35, are designated as 36. Herewith detector units are provided with different dimensions, as it will be discussed in detail with reference to FIG. 7. Said detector unit 4 can furthermore be preceded by a glass filter 37. To maintain suitable and stable conditions during detection a thermostatted filter holder is designated as 38.

In the again modified embodiment according to FIG. 4 again a device 2 for generating a plasma is employed, wherein device 2 is supplied with the plasma gas and the sample through the inlets 6 and 7 respectively. Said plasma production device 2 is followed by a collimating lens 3, whereafter the parallel ray beam formed by collimating lens 3 reaches a folding- or deflection mirror 39 and in consequence the parallel ray beam is supplied to a plurality of detector units, wherein similar to the previous embodiment interference filters 40 are followed by a plurality of lenses 32, by which fractional regions of parallel ray beam are each focused onto photodetectors 34, which in turn are connected through evaluation- or amplifier elements 36 to an electronic evaluation circuit 35.

Figure 5:
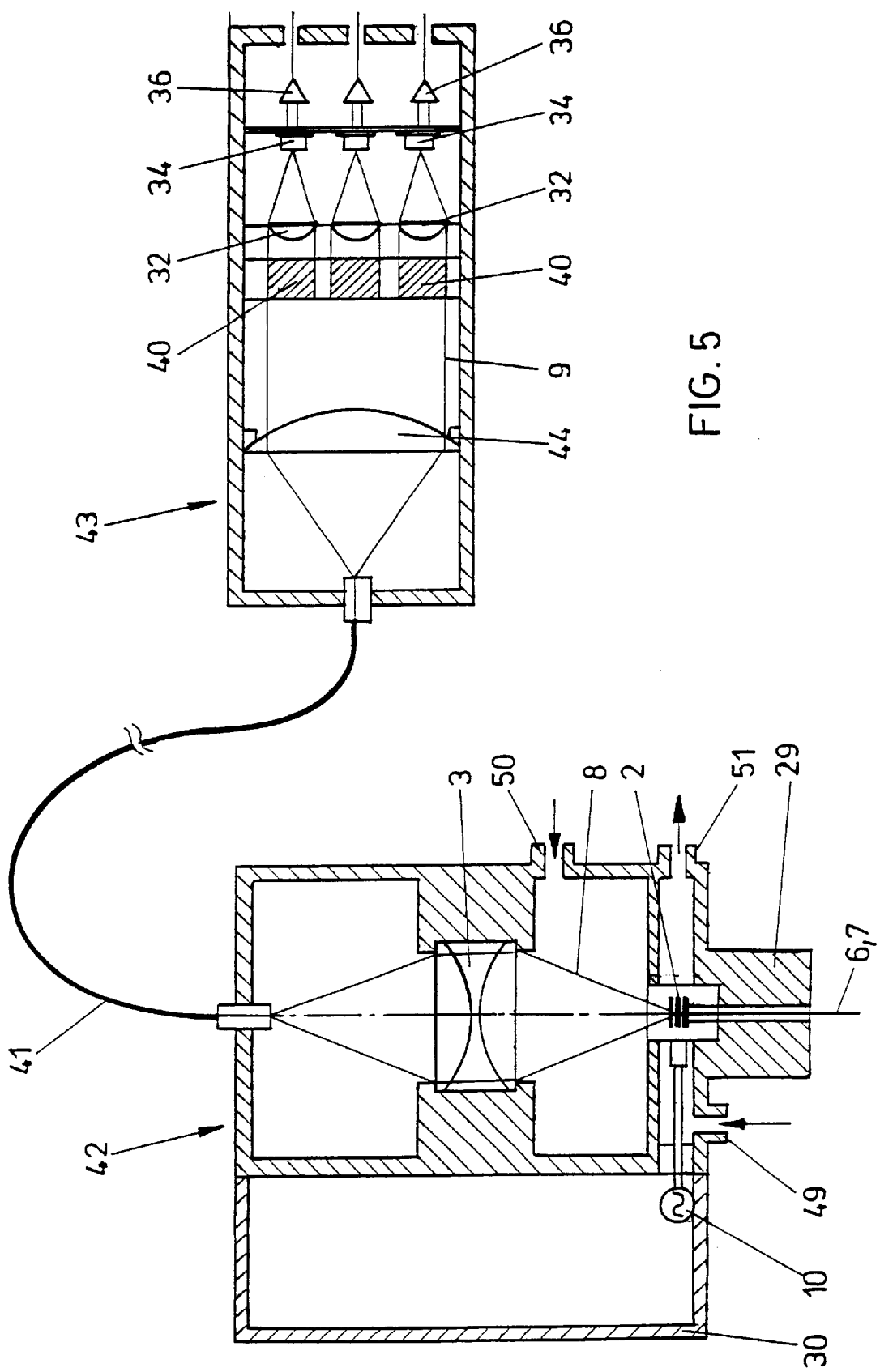
FIG. 5 shows a schematic representation in a partly sectional view of a further modified embodiment of a device according to the invention to analyze gaseous samples, wherein between the device for generating a plasma and the detector unit a fiber-optic link is provided.

In the embodiment schematically shown in FIG. 5 the device 2 for generating the plasma is followed by an optical unit 3 comprising a plurality of lenses, by which focusing of the emitted ray bundle 8 onto a fiber optics, generally designated as 41, is effected. It is therefore apparent that in the embodiment shown in FIG. 5 a partition of the device for analyzing gaseous samples into a unit 42, in which the production of the plasma occurs, and a unit 43 is effected, in which essentially a plurality of detector units is arranged, wherein in addition to the previous embodiments in unit 43 a suitable optical unit, for example a collimating lens 44, is provided to form a parallel ray beam, which subsequently, after passing interference filters 40 and lens assemblies 32 enables detection by a plurality of photodetectors 34 as well as subsequent evaluation in elements 35 and 36. Furthermore openings 49, 50 for the supply of a purge gas into the region of the device 2, as well as in front of the optical unit 3 are indicated, wherein a common outlet opening is designated as 51.

Instead of unit 43 shown in FIG. 5 of course any spectrometer, especially again fiber-optically coupled, for example a known mini-spectrometer employing photodetectors, can be put to use.

Figure 4:
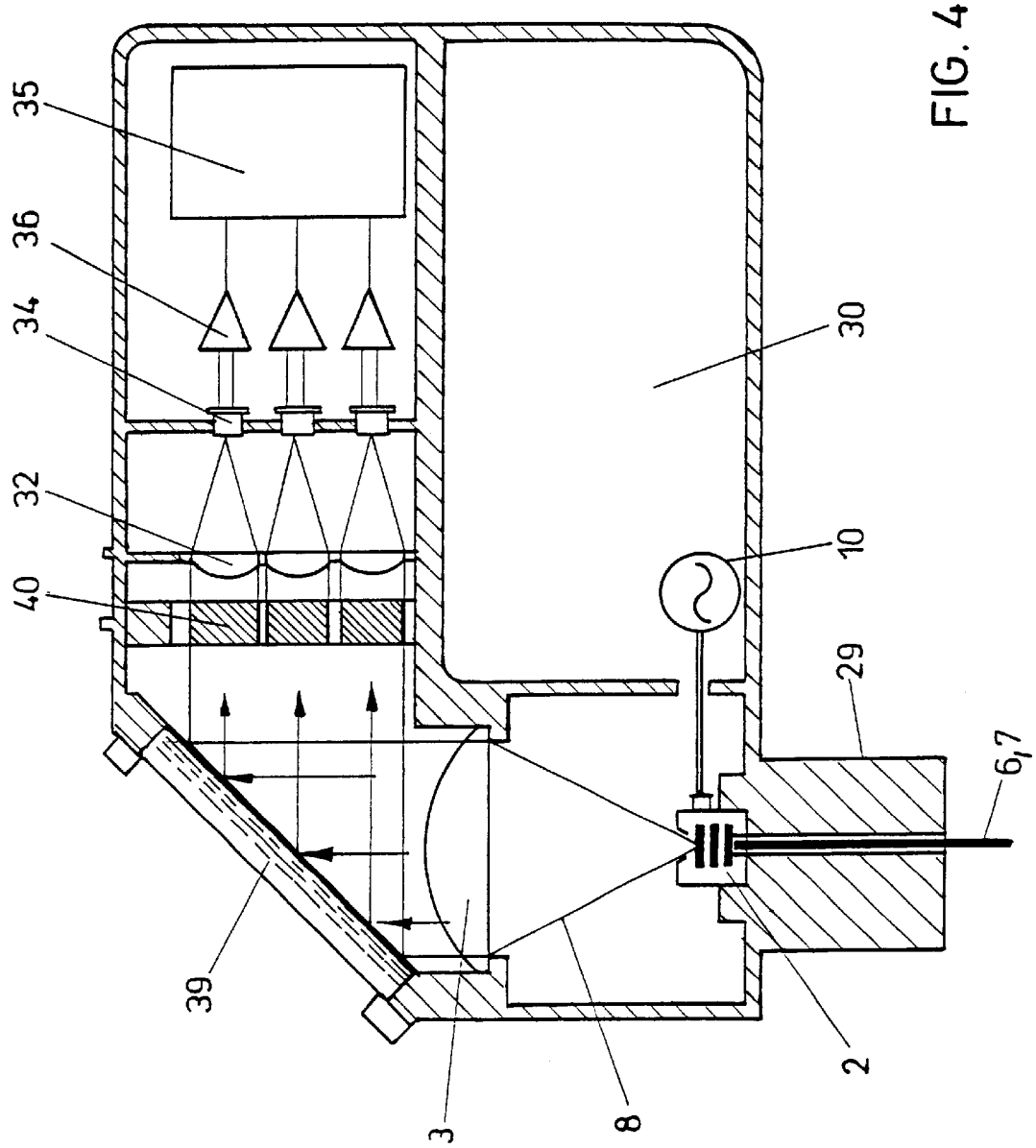
FIG. 4 shows a likewise schematic sectional view of a further modified embodiment of a device according to the invention to analyze gaseous samples.

FIGS. 6a and 6b schematically show the relative positioning of detector units, as they are outlined in the representations according to FIGS. 4 and 5. From FIG. 6a it can be seen that around an essentially centrally positioned detector unit 45 a plurality of equidistantly positioned detector units 46 is provided, wherein each of the detector units 45 and 46 again comprises an interference filter 40, a lens assembly 32 and a photodetector 34 with connectors or first evaluation units 36. Furthermore the interference filters 40 can again be preceded by a glass filter 37. With such an arrangement it is thus possible to simultaneously analyze and suitably process a plurality of different wavelengths, with simultaneous background correction if required.

From the representation according to FIGS. 7a and 7b it can be seen, that adjoining to a centrally positioned detector unit 47 having a relatively small sectional area a plurality of again equidistantly positioned detector units 48 is arranged, wherein each detector unit 48 again comprises an interference filter 40, a lens assembly 32 and a photodetector 34 with first evaluation or control units 36. The detector unit 47 is on the other hand, without lens assembly, only provided with a photodetector 34. Such an arrangement with a plurality of photodetectors is for example outlined in the embodiment according to FIG. 3. Also with such an arrangement of multiple detectors 47 and 48 it is possible to simultaneously detect and analyze a plurality of different wavelengths, wherein the small detector unit 47 in the center can for example serve for the measurement of oxygen as correction signal.

The evaluation of the signals of single detectors 34 in the schematically outlined evaluation units 35 takes place for example after separate measurement of various signal and background intensities by applying a background correction. Overall it can be seen, that by providing a plurality of detector units 45, 46, 47, 48, each in a compact unit, which can easily be exchanged, a multitude of data can be analyzed or evaluated simultaneously, with little space required.

Figure 8:
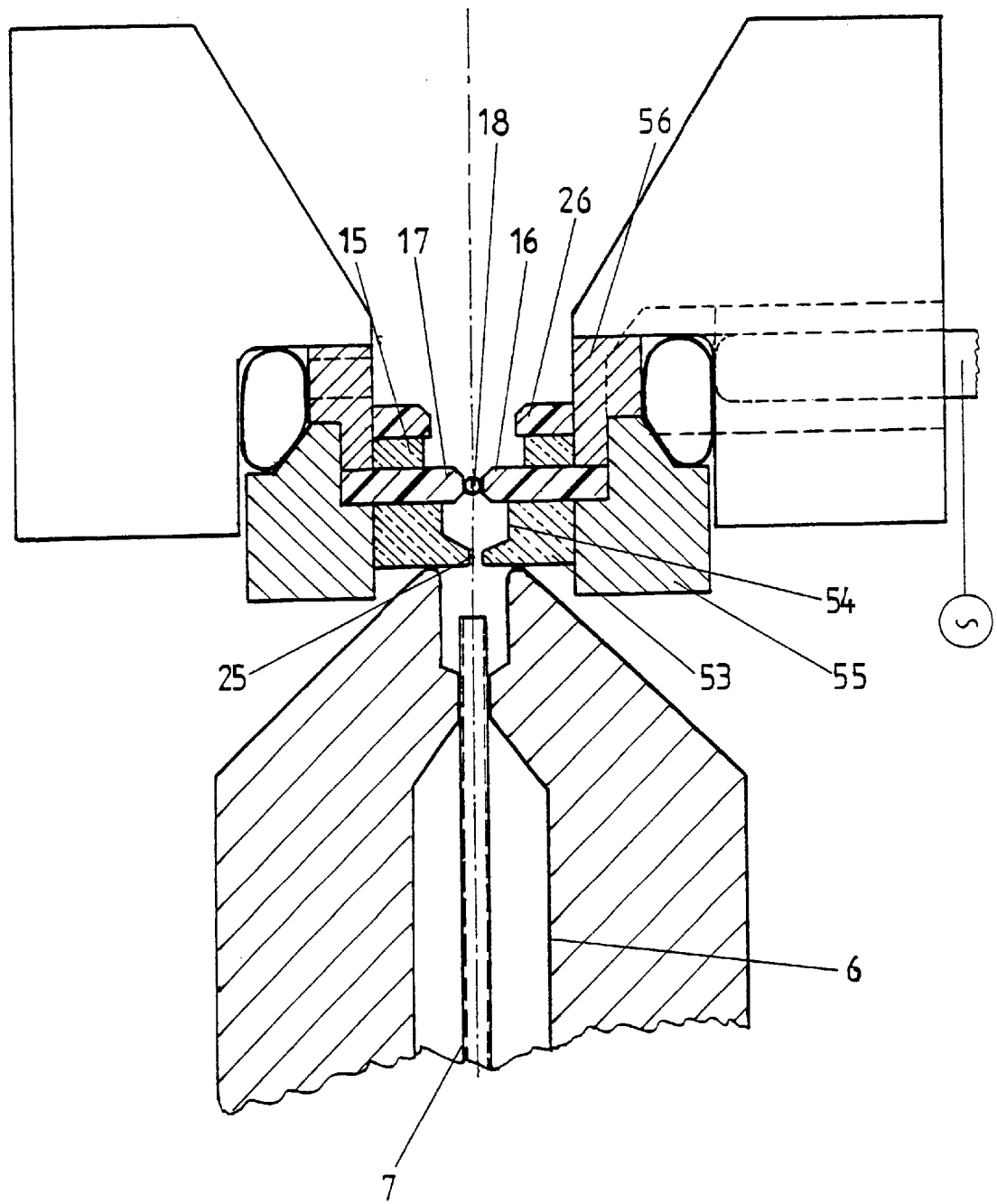
FIG. 8 shows, in a representation similar to FIG. 2, a section through a modified device for generating the plasma in a device according to the invention to analyze gaseous samples.

FIG. 8 shows in a representation similar to FIG. 2 a modified device 2 for generating a plasma in a device for analyzing gaseous samples, again in enlarged scale, wherein for same components the reference numbers of FIG. 2 have been retained. So the isolator 16 again has a through-opening 17 which in turn confines the plasma 18. The inlet for a sample is designated as 7. The isolator 16 for the confinement of said plasma 18 is again positioned between two ring- or disk-shaped electrodes, wherein the downstream electrode 15 again is formed similarly to the embodiment according to FIG. 2. In contrast to that embodiment the upstream electrode is combined with the isolator positioned upstream of the first electrode, wherein the resulting unit is designated as 53. The unit 53 again has an inlet- or through-opening 25, which corresponds essentially to the through-opening 17 of isolator 16 for confinement of plasma 18. Starting from the through-opening 25 of the unit 53 said unit is provided with a conically expanding or essentially pot-shaped cavity 54, such that overall, for the lines of electric flux to be formed between the electrodes to confine the plasma 18, a configuration essentially corresponding to the embodiment according to FIG. 2 results. Herewith the conically expanding or pot-like cavity 54 may be shaped, according to geometric requirements, having a depth corresponding to about twice its diameter.

The unit 53 formed by electrodes and isolators is again held in fixtures, which in the embodiment shown in FIG. 8 are designated as 55 and 56. From FIG. 8 it can be further seen that, divergent from the previous embodiments, the isolator 16 for the confinement of the plasma 18 extends to fixtures 55 or 56, such that overall in the embodiment shown in FIG. 8 a reduced number of components which have to conform to each other or be connected to each other, results.

What is claimed is:

1. Device for analyzing gaseous samples comprising a device for generating a plasma, a feeding device for the sample to be analyzed and at least one detector unit which comprises at least one interference filter, a lens arrangement and a photodetector for detecting radiation emitted by the sample to be analyzed, wherein the device for generating the plasma is made up of two ring-or disk-shaped parallel, interspaced electrodes, each having one essentially centrical, circular through-opening, and an isolator having a particularly circular through-opening for confining the plasma and wherein between said device for generating the plasma and the detector unit an optical unit for generating a parallel ray beam is provided.

2. Device as claimed in claim 1, wherein, viewed with respect to the direction of plasma gas flow, another isolator with a through-opening, which is essentially equivalent to said through-opening of said isolator positioned between said electrodes, is positioned upstream of said first electrode.

3. Device as claimed in claim 2, wherein the first electrode, viewed with respect to the direction of gas flow, and the isolator positioned upstream of it are combined into one single component and wherein the through-opening corresponding to said through-opening in the isolator confining said plasma is followed by a preferably conically expanding duct.

4. Device as claimed in claim 2, wherein an additional isolator is positioned downstream of the, viewed with respect to the direction of gas flow, second electrode, the through-opening of said isolator being slightly smaller than said through-opening of the adjacent electrode.

5. Device as claimed in claim 2, wherein the internal diameter of the through-opening in the isolator positioned downstream of said electrodes is at least two times the internal diameter of the through-opening in the isolator positioned upstream of said electrodes.

6. Device as claimed in claim 1, wherein said electrodes and isolators are either pressed together mechanically or are bonded together by metal-ceramic bonding.

7. Device as claimed in claim 1, wherein said electrodes and said device for generating the plasma are held in at least one fixture and are mounted in a gas-tight manner.

8. Device as claimed in claim 7, wherein the fixtures are equipped with centering mounts.

9. Device as claimed in claim 7, wherein said fixtures have outlets or purging holes for supplying an additive gas to plasma gas.

10. Device as claimed in claim 7, wherein the cavity housing said electrodes and/or said fixtures can be purged with a purge gas.

11. Device as claimed in claim 1, wherein the space between said device for generating the plasma and said optical unit can be purged with a purge gas.

12. Device as claimed in claim 1, wherein the power of the plasma is below 50 W.

13. Device as claimed in claim 1, wherein the excitation or operating frequency for said device for generating the plasma is selected to be at least 5 kHz.

14. Device as claimed in claim 1, wherein the plasma gas is selected from helium or argon.

15. Device as claimed in claim 1, wherein the pressure of the plasma gas is selected to be at least 0.01 bars.

16. Device as claimed in claim 1, wherein an additive gas is admixed to plasma gas at a level of at most 35 vol.-% and said additive gas is selected from $CO_2$, $N_2$, air, water vapor, hydrogen and oxygen.

17. Device as claimed in claim 1, wherein several detector units are arranged side by side and are illuminated by the parallel ray beam.

18. Device as claimed in claim 17, wherein a multitude of detector units are positioned each at the same distance from and around a centrally positioned detector unit.

19. Device as claimed in claim 18, wherein the centrally positioned detector unit has an area smaller than that of the other detector units.

20. Device as claimed in claim 1, wherein between said device for generating the plasma and the at least one detector unit a fiber-optic link is provided.

21. Device as claimed in claim 1, wherein between said device for generating the plasma and the at least one detector unit a deflecting or folding mirror is provided.

22. Device as claimed in claim 1, wherein said device for generating the plasma is coupled to an automatic control for switching off said device for generating the plasma as soon as a threshold value for the carbon signal is exceeded, and subsequent re-ignition of the same.

23. Device as claimed in claim 12, wherein the power of the plasma is between 3 and 30 W.

24. Device as claimed in claim 13, wherein the excitation or operating frequency for said device for generating the plasma is selected to be 50 kHz to 5 GHz.

25. Device as claimed in claim 13, wherein the excitation or operating frequency for said device for generating the plasma is selected to be above 10 MHz.

26. Device as claimed in claim 15, wherein the pressure of the plasma gas is selected to be between 0.1 and 0.5 bars.

27. Device as claimed in claim 16, wherein the additive gas is admixed to said plasma gas at a level less than 25 vol.-%.

28. Device as claimed in claim 1, wherein the optical unit is a collimator lens.

29. Device as claimed in claim 28, wherein the collimator lens is formed by an aspheric collimator lens of high aperture.

* * * * *